United States Patent [19]

Mues et al.

[11] 4,141,714
[45] Feb. 27, 1979

[54] FERTILIZERS FOR SUPPLYING PLANTS WITH MICRONUTRIENTS

[75] Inventors: Volker Mues, Wuppertal; Johannes Niggemann, Leverkusen, both of Fed. Rep. of Germany

[73] Assignee: Bayer Aktiengesellschaft, Leverkusen, Fed. Rep. of Germany

[21] Appl. No.: 869,885

[22] Filed: Jan. 16, 1978

[30] Foreign Application Priority Data

Feb. 4, 1977 [DE] Fed. Rep. of Germany ........ 2704681

[51] Int. Cl.$^2$ .................................... C05C; C07F 15/02
[52] U.S. Cl. ................................. 71/27; 71/DIG. 2; 260/439 R
[58] Field of Search ................... 71/27, 1, DIG. 2; 260/439 R, 439 CY

[56] References Cited

U.S. PATENT DOCUMENTS 4,047,921 9/1977 Mues ............................... 71/DIG. 2

FOREIGN PATENT DOCUMENTS 762414 11/1956 United Kingdom ............... 71/DIG. 2

OTHER PUBLICATIONS

Some Properties of the Monodentate Monoprotonated ... Complex Na$_2$ [Fe(CN)$_5$entt] 6H$_2$O, J. A. Olabe et al, Journal of Inorganic Nuclear Chem., 1974, vol. 36, pp. 1221–1226.

*Primary Examiner*—Richard V. Fisher
*Assistant Examiner*—Chris Konkol
*Attorney, Agent, or Firm*—Sprung, Felfe, Horn, Lynch & Kramer

[57] ABSTRACT

A fertilizer composition for supplying plants with nutrient iron containing as an active ingredient at least prussiate of the formula

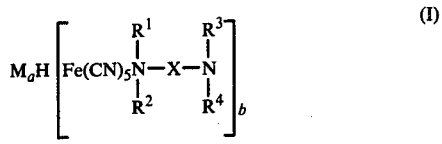

in which
M represents an alkali metal ion, alkaline earth metal ion, heavy metal ion or ammonium ion or a proton,
$R^1$, $R^2$, $R^3$ and $R^4$, independently of one another, each represent hydrogen, alkyl, hydroxyalkyl, cycloalkyl, optionally substituted aryl or aralkyl or
$R^1$, together with $R^2$, and/or $R^3$, together with $R^4$, represent an alkylene group, a bis-alkylene ether group or a bis-alkylene thioether group or, together with the adjacent nitrogen atom, form an unsaturated heterocyclic ring, or
$R^2$ and $R^4$ each represent hydrogen, alkyl or hydroxyalkyl and at the same time
$R^1$ and $R^3$ together represent an alkylene group,
X represents an alkylene group, hydroxyalkylene group, cycloalkylene group, bis-alkylenecycloalkylene group, bis-alkylene ether group, trisalkylene diether group, bis-alkylene thioether group or bis-alkyleneamino group,
a represents 1 or 2 and
b represents 1, 2, 3, or 4.

Also disclosed are certain new prussiates falling within the formula given above and their method of preparation.

33 Claims, No Drawings

4,141,714

FERTILIZERS FOR SUPPLYING PLANTS WITH MICRONUTRIENTS

BACKGROUND OF THE INVENTION

1. Field of the Invention

The present invention relates to the use as fertilizers of certain prussiates (prussides or pentacyanoferrates), some of which are known.

2. Discussion of the Prior Art

In order to achieve optimum growth conditions for a plant, in addition to the macronutrients, the micronutrients must also always be present in a substrate in a sufficient amount, and in particular in such a form that they can be taken up by the plant. It is therefore frequently necessary either to compensate a deficiency of micronutrients available to plants in substrates which are used for growing plants by adding appropriate micronutrient fertilizers, or to remedy the deficiency by converting the sparingly soluble micronutrient compounds contained in the substrate into more readily soluble substances. Fertilization with trace elements can thus be carried out in a variety of ways.

For example, it has been known for a long time that readily soluble salts of trace element cations with non-phytotoxic acids can be employed for supplying plants with the relevant micronutrients. Using conventional fertilizers of this type, it is indeed possible to achieve an effective micronutrient supply in weakly acid substrates or in substrates having a neutral reaction; however, their use in soils having a weekly basic reaction suffers from considerable disadvantages. Thus, the majority of polyvalent metal ions, in particular iron ions, cannot be taken up by the plants because, in a weakly alkaline substrate, these ions separate out in the form of sparingly soluble hydroxides and therefore do not contribute to plant nutrition.

Furthermore, it has been disclosed in "Der Vegetations-versuch" ("Vegetation Experiments") in "Methodenbuch" ("Book of Methods"), volume VIII, Neuman Verlag, Radebeul, Berlin, 1951, 180–194; Plant Physiology 26, 411 (1951); Soil Science 80, 101–108 (1955) and "Organic Sequestering Agents", John Wiley and Sons, Inc. New York, 1959, 455–469, that the plants can be supplied with the necessary micronutrient cations in the form of chelate complexes of citric acid, gluconic acid, nitrilotriacetic acid, ethylenediaminetetraacetic acid and ethylenediamine-N,N'-di-(o-hydroxyphenyl)-acetic acid. With the aid of complexes of this type it is possible to achieve a supply of micronutrients to the plants not only in weakly acid or neutral soils but also, to a certain degree, in weakly alkaline soils because, as a result of the relatively high stability of these complexes, an undesired precipitation of the micronutrient cations in the neutral or weakly basic medium is largely prevented. Nevertheless, the use of chelate complexes for the indicated purpose suffers from some disadvantages. Thus, the duration of action of chelate complexes of citric acid or gluconic acid is only relatively short, since these naturally occurring acids can be degraded fairly rapidly by soil micro-organisms.

The chelate complexes of the synthetic aminopolycarboxylic acids, with the exception of the iron complex of ethylenediamine-N,N'-di-(o-hydroxyphenyl)-acetic acid, which is important for combating chlorosis, can be employed only with limitations in strongly alkaline soils, because the stability of the complexes does not always suffice to avoid the micronutrient cations being immobilised in the form of sparingly soluble hydroxides or oxides. A further disadvantage is that the aminopolycarboxylic acids form very stable, highly toxic and at the same time water-soluble chelate complexes with the heavy metal ions of cadmium, lead and mercury, which can be contained in the soil in the form of almost insoluble compounds. Since these heavy metal ion complexes can, because of their good solubility, pass into the soil water, the use of aminopolycarboxylic acids is not acceptable for toxicological reasons. It is true that the iron complex of ethylenediamine-N,N'-di-(o-hydroxyphenyl)-acetic acid is, as already mentioned, of practical importance in combating chlorosis. However, it is a disadvantage that this substance can be prepared only with relative difficulty and is furthermore not light-stable.

SUMMARY OF THE INVENTION

It has now been found, that the prussiates of the general formula

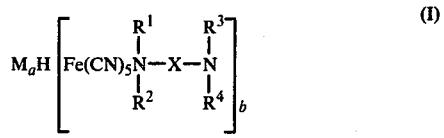

(I)

in which

M represents an alkali metal ion, alkaline earth metal ion, heavy metal ion or ammonium ion or a proton, (A) $R^1$, $R^2$, $R^3$ and $R^4$, independently of one another, each represent hydrogen, alkyl, hydroxyalkyl, cycloalkyl, optionally substituted aryl or aralkyl, or (B) $R^1$, together with $R^2$, and/or $R^3$, together with $R^4$, represent an alkylene group, a bis-alkylene ether group or a bis-alkylene thioether group or, together with the adjacent nitrogen atom, form an unsaturated heterocyclic ring, or (C) $R^2$ and $R^4$ each represent hydrogen, alkyl or hydroxyalky and at the same time $R^1$ and $R^3$ together represent an alkylene group, X represents an alkylene group, hydroxyalkylene group, cycloalkylene group, bis-alkylenecycloalkylene group, bis-alkylene ether group, tris-alkylene diether group, bis-alkylene thioether group or bis-alkyleneamino group, a represents 1 or 2 and b represents 1, 2, 3 or 4, and hydrates of the compounds of the formula (I), are very suitable for supplying plants with the micronutrient iron.

The present invention therefore provides a fertilizer composition for supplying plants with the micronutrient iron, which comprises, as active ingredient, at least one prussiate of the formula (I), or a hydrate thereof, in admixture with a solid or liquefied gaseous diluent or carrier or in admixture with a liquid diluent or carrier containing a surface-active agent.

The present invention also provides a method of supplying plants with the micronutrient iron, which comprises applying to the plants, or to the substrate in which they grow, a prussiate of the formula (I), or a hydrate thereof, alone or in admixture with a diluent or carrier.

The outstanding activity of the substances to be used according to the invention in supplying plants with the trace element iron is to be regarded as very surprising since it was to be assumed, in view of the state of the art, that the substances according to the invention are only of poor stability for the purpose indicated because, compared with aminopolycarboxylic acids, they contain iron in a very highly complexed form. Contrary to expectations, however, the substances according to the invention have a very good activity in micronutrient fertilization.

It is particularly advantageous that the substances according to the invention do not form stable complexes with the heavy metal ions of cadmium, lead and mercury present in the soil. Hence, the use of the prussiates for supplying plants with the micronutrient iron is also acceptable on toxicological grounds. The substances according to the invention thus represent a valuable enrichment of the art.

The formula (I) provides a general definition of the prussiates which can be used according to the invention. However, they can also be characterized by the formula

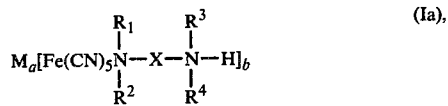

in which M, $R^1$, $R^2$, $R^3$, $R^4$, a and b have the meanings stated above, but it is not possible in every case to determine unambiguously to which nitrogen atom the proton is attached. For reasons of simplicity, the prussiates to be used according to the invention are in each case written in the "cation proton form", corresponding to the formula (I), in the following text.

Preferably, in the formula (I), R represents sodium, potassium, magnesium, calcium, barium, ammonium or hydrogen;

$R^1$ represents hydrogen, straight-chain or branched alkyl or hydroxyalkyl each with 1 to 6, especially 1 to 4, carbon atoms, cyclopentyl, cyclohexyl, benzyl or phenyl which is optionally substituted by alkyl with 1 to 4 carbon atoms and/or halogen, and $R^2$, $R^3$ and $R^4$, which need not be identical, each represent hydrogen, straight-chain or branched alkyl with 1 to 6, especially 1 to 4, carbon atoms, or phenyl which is optionally substituted by alkyl with 1 to 4 carbon atoms and/or halogen; or $R^1$, together with $R^2$, and/or $R^3$, together with $R^4$, represent a straight-chain or branched alkylene group with 1 to 7 carbon atoms or a bis-alkylene ether or bis-alkylene thioether group each with 1 to 4 carbon atoms per alkylene grouping; or $R^1$ and $R^2$ and/or $R^3$ and $R^4$ represent, together with the adjacent nitrogen atom, a five-membered to seven-membered unsaturated heterocyclic ring in which up to 3 carbon atoms can be replaced by nitrogen; or $R^1$ and $R^3$ together represent a straight-chain or branched alkylene group with 1 to 3 carbon atoms;

X represents an alkylene or hydroxyalkylene group with 1 to 15 carbon atoms, cyclohexylene, a bis-alkylene-cyclohexylene group with 1 to 4 carbon atoms per alkylene grouping or a bis-alkylene ether, tris-alkylene diether, bis-alkylene thioether or bis-alkyleneamino group with 1 to 4 carbon atoms per alkylene group;

a represents 1 or 2; and b represents 1, 2 or 3.

The numbers for a and b are calculated from the sum of the charges of the five negatively charged cyanide ions, the doubly or triply positively charged iron cation, the proton and the neutral radical

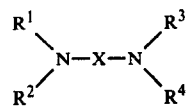

and from the valency of the cation M.

Examples which may be mentioned of the prussiates of the formula (I) which can be used according to the invention are: disodium hydrogen (1,2-diaminoethane)-pentacyanoferrate-II, disodium hydrogen (N-methyl-1,2-diaminoethane)-pentacyanoferrate-II, disodium hydrogen (N-ethyl-1,2-diaminoethane)-pentacyanoferrate-II, disodium hydrogen (N-isopropyl-1,2-diaminoethane)-pentacyanoferrate-II, disodium hydrogen (N-phenyl-1,2-diaminoethane)-pentacyanoferrate-II, disodium hydrogen (N,N'-dimethyl-1,2-diaminoethane)-pentacyanoferrate-II, disodium hydrogen (N,N-dimethyl-1,2-diaminoethane)-pentacyanoferrate-II, disodium hydrogen (N,N-diethyl-1,2-diaminoethane)-pentacyanoferrate-II, disodium hydrogen (1,2-diaminocyclohexylene)-pentacyanoferrate-II, disodium hydrogen (N,N'-diethyl-1,2-diaminoethane)-pentacyanoferrate-II, disodium hydrogen (N,N-dimethyl-N'-ethyl-1,2-diaminoethane)-pentacyanoferrate-II, disodium hydrogen (1,2-dianilinoethane)-pentacyanoferrate-II, disodium hydrogen (N-benzyl-N,N'-dimethyl-1,2-diaminoethane)-pentacyanoferrate-II, disodium hydrogen (N,N,N'-trimethyl-1,2-diaminoethane)-pentacyanoferrate-II, disodium nitrogen (N,N,N'-triethyl-1,2-diaminoethane)-pentacyanoferrate-II, disodium hydrogen (N,N,N',N'-tetramethyl-1,2-diaminoethane)-pentacyanoferrate-II, disodium hydrogen (N,N,N',N'-tetraethyl-1,2-diaminoethane)-pentacyanoferrate-II, disodium hydrogen [N-(2-aminoethyl)-piperidine]-pentacyanoferrate-II, disodium hydrogen [N-(2-aminoethyl)-pyrrolidine]-pentacyanoferrate-II, disodium hydrogen [N-(2-aminoethyl)-2-imidazolidone]-pentacyanoferrate-II, disodium hydrogen [N-(2-aminoethyl)-piperazine]-pentacyanoferrate-II, disodium hydrogen [N-(2-aminoethyl)-morpholine]-pentacyanoferrate-II, disodium hydrogen (1,2-dipiperidinoethane)-pentacyanoferrate-II, disodium hydrogen (1,2-dimorpholinoethane)-pentacyanoferrate-II, disodium hydrogen (N-β-hydroxyethyl)-1,2-diaminoethane)-pentacyanoferrate-II, disodium hydrogen (piperazine)-pentacyanoferrate-II, disodium hydrogen (N-methylpiperazine)-pentacyanoferrate-II, disodium hydrogen (N-N'-dimethylpiperazine)-pentacyanoferrate-II, disodium hydrogen (N-β-hydroxyethylpiperazine)-pentacyanoferrate-II, disodium hydrogen (1,2-diaminopropane)-pentacyanoferrate-II, disodium hydrogen [1-(2-aminopropyl)-piperidine]-pentacyanoferrate-II, disodium hydrogen (2,5-dimethylpiperazine)-pentacyanoferrate-II, disodium hydrogen (2-methylamino-1-ethyl-pyrrolidine)-pentacyanoferrate-II, disodium hydrogen (1,3-diaminopropane)-pentacyanoferrate-II, disodium hydrogen (N-methyl-1,3-diaminopropane)-pentacyanoferrate-II, disodium hydrogen (N,N-dimethyl-1,3-diaminopropane)-pentacyanoferrate-II, disodium hydrogen (N,N'-diethyl-1,3-diaminopropane)-pentacyanoferrate-II, disodium hydrogen (N-cyclohexyl-1,3-diaminopropane)-pentacyanoferrate-II, disodium hydrogen [N-(3-aminopropyl)-morpholine]-pentacyanoferrate-II, disodium hydrogen [N-(3-aminopropyl)-2-pyrrolidine]-pentacyanoferrate-II, disodium hydrogen [N-(3-aminopropyl)-diethanolamine]-pentacyanoferrate-II, disodium hydrogen [N,N'-bis-(3-aminopropyl)-piperazine]-pentacyanoferrate-II, disodium hydrogen (N,N,N',N'-tetramethyl-1,3-diaminopropane)-pentacyanoferrate-II, disodium [N-(β-hydroxyethyl)-1,3-diaminopropane]-pentacyanoferrate-II, disodium hydrogen (1,3-diamino-2-hydroxypropane)-pentacyanoferrate-II, disodium hydrogen (1,2-diamino-2-methylpropane)-pentacyanoferrate-II, disodium hydrogen (N-isopropyl-2-methyl-1,2-diaminopropane)-pentacyanoferrate-II, disodium hydrogen (1,4-diaminobutane)-pentacyanoferrate-II, disodium hydrogen (1,4-diaminocyclohexylene)-pentacyanoferrate-II, disodium hydrogen (N,N,N',N'-tetramethyl-1,4-diaminobutane)-pentacyanoferrate-II, disodium hydrogen (4-aminomethyl-2,2,6,6-tetramethylpiperidine)-pentacyanoferrate-II, disodium hydrogen (4-aminomethylpiperidine)-pentacyanoferrate-II, disodium hydrogen (1,5-diaminopentane)-pentacyanoferrate-II, disodium hydrogen (2-amino-5-diethylaminopentane)-pentacyanoferrate-II, disodium hydrogen [1,3-bis-(aminomethyl)-cyclohexane]-pentacyanoferrate-II, disodium hydrogen (1,6-diaminohexane)-pentacyanoferrate-II, disodium hydrogen (N,N'-dimethyl-1,6-diaminohexane)-pentacyanoferrate-II, disodium hydrogen (N,N,N',N'-tetramethyl-1,6-diaminohexane)-pentacyanoferrate-II, disodium hydrogen (1,7-diaminoheptane)-pentacyanoferrate-II, disodium hydrogen (1,8-diaminooctane)-pentacyanoferrate-II, disodium hydrogen (1,8-diamino-p-methane)-pentacyanoferrate-II, disodium hydrogen (1,9-diaminononane)-pentacyanoferrate-II, disodium hydrogen (2,5-diamino-2,5-dimethylhexane)-pentacyanoferrate-II, disodium hydrogen (1,10-diaminodecane)-pentacyanoferrate-II, disodium hydrogen (1,12-diaminododecane)-pentacyanoferrate-II, disodium hydrogen [2,2'-oxy-bis-(ethylamine)]-pentacyanoferrate-II, disodium hydrogen [2,2'-oxy-bis-(N,N-dimethylethylamine)]-pentacyanoferrate-II, disodium hydrogen [1,4-butanediol-bis-(3-aminopropyl ether)]-pentacyanoferrate-II, disodium hydrogen (diethylenetriamine)-pentacyanoferrate-II, disodium hydrogen (triethylenetetramine)-pentacyanoferrate-II, disodium hydrogen [N,N-bis-(2-aminoethyl)-methylamine]-pentacyanoferrate-II, disodium hydrogen [bis-(β-dimethylaminoethyl)-methylamine]-pentacyanoferrate-II, disodium hydrogen [N-(2-aminoethyl)-1,3-diaminopropane]-pentacyanoferrate-II, disodium hydrogen (2-[2-(2-aminoethylamino)-ethylamino]-ethanol)-pentacyanoferrate-II, disodium hydrogen [bis-(3-aminopropyl)-aminoethanol]-pentacyanoferrate-II, disodium hydrogen [bis-(3-aminopropyl)-methylamine]-pentacyanoferrate-II, disodium hydrogen (N-methyl-N-β-hydroxyethyl-1,3-diaminopropane)-pentacyanoferrate-II and disodium hydrogen (N,N,N',N'-tetramethyl-1,3-diamino-2-hydroxypropane)-pentacyanoferrate-II. The hydrates of these prussiates may also be used.

Of the prussiates to be used according to the invention, only one compound is already known from the literature (see Chemische Berichte 46, 3514 (1913) and J. inorg. nucl, Chem. 1974, volume 36, pages 1221-1226). The substance concerned is characterised, on the basis of spectroscopic and magnetic data, as disodium (2-aminoethylammonium)-pentacyanoferrate-II. However, the remaining prussiates according to the invention are new.

Accordingly, the present invention also provides, as new compounds, the prussiates of the general formula

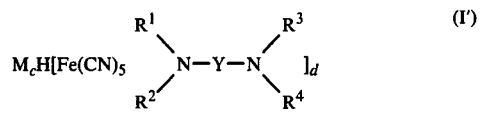

in which

M represents an alkali metal ion, alkaline earth metal ion, heavy metal ion or ammonium ion or a proton, c represents 1 or 2, d represents 1, 2, 3 or 4, $R^1$, $R^2$, $R^3$ and $R^4$, independently of one another, each represent hydrogen, alkyl, hydroxyalkyl, cycloalkyl, optionally substituted aryl or aralkyl, or $R^1$, together with $R^2$, and/or $R^3$, together with $R^4$, represent an alkylene, a bis-alkylene ether or a bis-alkylene thioether group or, together with the adjacent nitrogen atom, form an unsaturated heterocyclic ring, or $R^2$ and $R^4$ represent hydrogen, alkyl or hydroxyalkyl and at the same time $R^1$ and $R^3$ together represent an alkylene group, and Y represents an alkylene group, hydroxyalkylene group, cycloalkylene group, bis-alkylenecycloalkylene group, bis-alkylene ether group, trisalkylene diether group, bis-alkylene thioether group or bis-alkyleneamino group, except that Y does not represent a —$CH_2$—$CH_2$— group when M represents sodium $R^1$, $R^2$, $R^3$ and $R^4$ each represent hyrogen, c represents 2 and d represents 1, and their hydrates.

The invention also provides a process for the preparation of a prussiate of the formula (I'), in which a compound of the general formula

in which

M, c and d have the meanings stated above, is reacted with a compound of the general formula

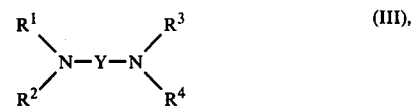

in which $R^1$, $R^2$, $R^3$, $R^4$ and Y have the meanings stated above, in a aqueous solution, optionally in the presence of a buffer and optionally in the presence of an additional diluent.

If sodium nitroprusside and ethylenediamine are used as the starting materials, the course of the reaction can be represented by the following equation:

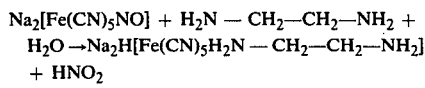

The formula (II) provides a general definition of the prussiates required as starting materials. In the formula (II), M preferably represents those cations which have already been mentioned as preferred for M in connection with the formula (I). In the formula (II), c preferably represents 1 or 2 and d preferably represents 1, 2 or 3. The numbers for c and d are calculated from the sum of the charges of the five negatively charged cyanide ions, the doubly or triply positively charged iron cation, the positively charged nitrosyl ion and from the valency of the cation M.

The prussiates of the formula (II) are known or can be prepared by methods which are known in principle.

The formula (III) provides a general definition of the compounds which are also required as starting materials. In the formula (III), $R^1$, $R^2$, $R^3$ and $R^4$ preferably represent those radicals which have already been mentioned as preferred for $R^1$, $R^2$, $R^3$ and $R^4$ in connection with the formula (I). The radical Y preferably represents those radicals which have already been mentioned as preferred for X. However, the limitation that Y does not present the —$CH_2$—$CH_2$—group when M represents sodium, $R^1$, $R^2$, $R^3$ and $R^4$ each represent hydrogen, c represents 2 and d represents 1 applies here.

The compounds of the formula (III) are known or can be prepared by methods which are known in principle.

The process according to the invention is carried out in an aqueous solution. It is possible to add additional diluents to the aqueous solution. Such diluents which can be used are all the inert water-miscible organic solvents, especially methanol and ethanol.

Possible buffers which can be used in the reaction according to the invention are all the customary buffer systems. Sodium acetate may be mentioned as being preferred. If the reaction is carried out in the presence of a buffer, it is advisable to employ a buffer, the cation of which is identical to that of the compound to be prepared, in order to avoid troublesom side reactions.

The reaction temperature can be varied within a relatively wide range. In general, the reaction is carried out at temperatures between 0° C. and 50° C., preferably between 5° C. and 30° C.

In carrying out the process according to the invention, 1 mole or a slight excess of a compound of the formula (III) is employed per mole of a nitroprussiate of the formula (II). The reaction products are isolated according to customary methods. In general, the procedure is to add a water-miscible inert organic solvent in which the compounds of the formula (I) are not very soluble to the reaction mixture. In this procedure, the compounds of the formula (I) or their hydrates then separate out in the crystalline form or as slowly crystallising oils.

The prussiates of the formula (I) and their hydrates are very suitable for supplying plants with the micronutrient iron. Furthermore, they can be used for combating and curing iron deficiency diseases in plants.

However, they can also be used for combating other plant deficiency diseases, such as, for example, "little leaf", "gray speck disease", "reclamation disease"and "white bud disease", if they contain those nutrient ions, a deficiency of which the relevant plant diseases can be attributed to.

The prussiates of the formula (I) which can be used according to the invention psssess only a slight phytotoxicity and are therefore well tolerated by plants.

Plants which are prone to deficiency diseases, in particular iron deficiency diseases (iron deficiency chloroses), include: species of cerals (for example rice, maize and millet), tuber and root crops (for example sugarbeet), oleaginous fruits (for example soybean, groundnut, olive and sunflower), table fruit (for example peach, pear, apple, apricot, plum, cherry, quince, citrus fruit, grape, hazelnut, walnut, currant, goosebery, raspberry, blackberry, bilberry, pineapple and avocado), vegetables (for example lettuce, broad bean, pea, tomato and melon), ornamental trees and shrubs (for example rose, eucalyptus, liquidamber, mimosa, elm, catalpa, spirea, pyracantha, juniperus, ligustrum, hibiscus, syringa and hydrangea), perennials (for example delphinium, primula, paenia, papaver, anthirrhinum, iris and lupine), pot plants and annuals (for example pelargonium, petunia, gardenia, calceolaria, chrysanthemum, camellia and begonia), peat-loving plants (for example azalea, rhododendron, erica and skimmia) and grasses (for example lawn grasses).

The active compounds can be converted into the customary formulations, such as solutions, emulsions, suspensions, powders, pastes and granules.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylene or methylene chloride, aliphatic or alicyclic hydrocarbons, such as cyclohexane or paraffins, for cxample mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground syntetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

The substances to be used according to the invention, for supplying plants with the micronutrient iron, can be present in the formulations as a mixture with other fertilizers or pesticidal active compounds. In general, the formulations contain from 0.1 to 95 percent by weight of active compound, preferably from 0.5 to 90 percent by weight.

The active compounds can be used as such, in the form of their formulations or as the use forms prepared therefrom, such as ready-to-use solutions, emulsions, foams, suspensions, powders, pastes and granules. They may be used in accordance with the methods customary in agriculture and in horticulture, for example by direct introduction into the soil, by watering, spraying, atomising, scattering or dusting. Special types of application which may be mentioned are root application, leaf application, stem application, stem injection and bark application. In the case of root application, the fertilizer can either be mixed with the culture substrate or can be introduced into furrows in the soil. Furthermore, it is possible to introduce the fertilizer into the lower root region with the aid of a fertilizer lance or through punched or drilled holes. As a rule, application to the leaf is effected by spraying the plants with a fertilizer solution or dipping plants or parts of plants into a fertilizer solution. In the case of stem injection, the fertilizer is directly introduced into the plants, particularly trees, through bore-holes in trunks or branches. Bark application can be effected by spraying the bare wood with the fertilizer solution, or by placing bands, for example of textile, paper or foamed plastic, impregnated with nutrients, on tree trunks or branches, if appropriate after partial or complete removal of the layer of bark or cork in the treatment zone. Application to the bark with the aid of pastes containing nutrient is also possible.

It is also possible to apply the prussiates (I) or their hydrates by the ultra-low volume (ULV) method. Furthermore, the prussiates which can be used according to the invention can be absorbed on ion exchangers and employed in this form as fertilizers.

The amount of the prussiate or its hydrate which is employed can be varied within a relatively wide range. It depends essentially on the nature of the soil and on the nutrient requirement of the particular plant. In general, the amounts of active compound used are from 0.1 to 100 kg/ha, preferably from 1 to 50 kg/ha.

The good activity of the prussiates to be used according to the invention in supplying plants with micronutrients can be seen from the examples which follow.

In these Examples, the compounds according to the present invention are each identified by the number (given in brackets) of the corresponding preparative Example, which will be found later in this specification.

The known comparison compounds are identified as follows:

(A) = FeSO$_4$ . 7H$_2$O (B) = an iron chelate complex of ethylenediamine-N,N'-di-(o-hydroxyphenyl) acetic acid, as the commercially available iron fertilizer "Sequestrene 138 Fe".

EXAMPLE A

Combating Iron Deficiency/Root Uptake Test/Greenhouse

Test Plant: Grape (variety: Müller Thurgau)

Culture substrate: Mixture of polystyrene foam flock (Styromull) and potassium alginate in the volume ratio of 10:1

Test plants were grown in a culture substrate of the composition indicated above, fertilisation and watering being effected by adding, twice weekly, a mineral iron deficient nutrient solution according to Hoagland and Arnon (Circular 347, College of Agriculture, University of California, Berkeley 1950). The completely chlorotic test plants grown in this way were transplanted, at the five-leaf stage, into another culture substrate of the composition indicated above, to which, however, the particular desired amount of iron fertiliser had been admixed. During the further growth, fertilisation and watering were effected in the same way as during the initial growth.

The evaluation was made when an average of 2 leaves had newly formed on the plants treated with an optimum amount of a water-soluble, commercially available iron fertiliser. In each case the average number of newly formed leaves was determined on all the test plants. Furthermore, the intensity of the green colour of newly formed leaves was rated on the following scale:

1 = 0% chlorotic (dark green)
3 = 25% chlorotic
5 = 50% chlorotic
7 = 75% chlorotic
9 = 100% chlorotic (corresponding to the untreated control plants)

The nutrients, the nutrient concentrations and the test results can be seen from the table which follows:

Table A

| Combating iron deficiency/root uptake test greenhouse Test plant:Grape/variety: Müller-Thurgau | | | | |
|---|---|---|---|---|
| Nutrient formulation | Water solubility of the formulation | Nutrient formulation concentration in the substrate [mg/l] | Intensity of the green colour of young leaves | Average number of newly formed leaves |
| — (control) | — | — | 9 | 0 |
| (A) | complete | 15 | 9 | 0 |
| (B) | complete | 50 | 3 | 2 |
| (3) | complete | 32 | 2 | 3 |
| (4) | complete | 33 | 2 | 5 |
| (6) | complete | 33 | 2–3 | 3 |
| (8) | complete | 35 | 2 | 3 |
| (1) | complete | 32 | 1–2 | 6 |
| (9) | complete | 32 | 2 | 3 |
| (11) | complete | 33 | 2 | 2 |
| (12) | complete | 17 | 2 | 2 |
| (13) | complete | 9 | 2 | 3 |

EXAMPLE B

Combating Iron Deficiency/Root Uptake Test/Greenhouse

Test plant: *Chrysanthemum indicum* (variety: Yellow Delaware)

Culture substrate: Mixture of polystyrene foam flock (Styromull) and potassium alginate in the volume ratio of 10:1.

test plants were grown in a culture substrate of the composition indicated above, fertilisation and watering being effected by adding, twice weekly, a mineral iron deficient nutrient solution according to Hoagland and Arnon (Circular 347), College of Agriculture, University of California, Berkeley 1950). The completely chlorotic test plants grown in this way were transplanted, at the five-leaf stage, into another culture substrate of the composition indicated above, to which, however, the particular desired amount of iron fertiliser had been admixed. During the further growth, fertilisation and watering were effected in the same way as during the initial growth.

The evaluation was made when an average of 5 leaves had newly formed on the plants treated with an optimum amount of a water-soluble commercially available iron fertiliser. In each case the average number of newly formed leaves was determined on all the test plants. Furthermore, the intensity of the green colour of newly formed leaves was rated on the following scale:

disodium hydrogen (1,2-diaminopropane)-pentacyanoferrate with a melting point >300° C.

The compounds listed in Table 1 which follos were prepared in an analogous manner:

Table 1

| Example | Structural formula | Melting point [° C] |
|---|---|---|
| 2 | $Na_2H[Fe(CN)_5NH_2-CH_2-CH_2NH_2] \cdot 6 H_2O$ | >300 |
| 3 | $Na_2H[Fe(CN)_5NH_2(CH_2)_3N(C_2H_5)_2]$ | >300 |
| 4 | $Na_2H[Fe(CN)_5NH_2-CH_2-CH_2-CH_2-N(CH_3)_2]$ | >300 |
| 5 | $Na_2H[Fe(CN)_5NH_2(CH_2)_3NH-CH_3]$ | >300 |
| 6 | $Na_2H[Fe(CN)_5NH_2-CH_2-CH_2-NH-CH_3]$ | >300 |
| 7 | $Na_2H[Fe(CN)_5NH_2CH_2-CH_2-NH-CH_2-CH_2-NH_2]$ | >300 |
| 8 | $Na_2H[Fe(CN)_5NH-CH_2-CH_2-NH-CH_3]$ with $CH_3$ substituent | >300 |
| 9 | $Na_2H[Fe(CN_5NH_2(CH_2)_4-NH_2]$ | >300 |
| 10 | $Na_2H[Fe(CN)_5NH_2(CH_2)_6-NH_2]$ | >300 |
| 11 | $Na_2H[Fe(CN)_5NH_2-CH-(CH_2)_3-N(C_2H_5)_2]$ with $CH_3$ substituent | >300 |
| 12 | $Na_2H[Fe(CN)_5NH_2-(CH_2)_3-NH-\langle H \rangle]$ | >300 |
| 13 | $Na_2H[Fe(CN)_5NH_2-\langle H \rangle-NH_2]$ | >300 |

1 = 0% chlorotic (dark green)
3 = 25% chlorotic
5 = 50% chlorotic
7 = 75% chlorotic
9 = 100% chlorotic (corresponding to the untreated control plants)

The nutrients, the nutrient concentrations and the test results can be seen from the table which follows:

TABLE B

Combating iron deficiency/root uptake test/ greenhouse
Test plant: *Chrysanthemum indicum*
variety: Yellow Delaware

| Nutrient formulation | Water-solubility of the formulation | Nutrient formulation concentration in the substrate [mg/l] | Intensity of the green colour of young leaves | Average number of newly formed leaves |
|---|---|---|---|---|
| — (control) | — | — | 9 | 0 |
| (A) | complete | 15 | 9 | 0 |
| (B) | complete | 50 | 1–2 | 5 |
| (4) | complete | 50 | 1–2 | 5 |
| (3) | complete | 50 | 2 | 5 |
| (6) | complete | 50 | 2 | 5 |
| (1) | complete | 50 | 2 | 4 |
| (12) | complete | 50 | 2 | 5 |

Preparative examples

EXAMPLE 1

$$Na_2H[Fe(CN)_5H_2N-CH_2-CH(NH_2)-CH_3] \quad (1A)$$

59.6 g (0.2 mol) of sodium nitroprusside and 30 g (0.2 mol) of sodium acetate hydrate were dissolved in 90 ml of water. A solution of 15.5 g (0.21 mol) of 1,2-diaminopropane in 75 ml of ethanol was added dropwise, whilst cooling slightly, a further 75 ml of ethanol were then added and the mixture was subsequently stirred for 2 hours at room temperature and poured into ethanol. The product, which had initially separated out as an oil, crystallised on grinding. It was filtered off, washed with ethanol and dried. This gave 28.5 g (46% of theory) of

What we claim is:

1. A fertilizer composition for supplying plants with the micronutrient iron, comprising an effective amount of at least one prussiate of the general formula

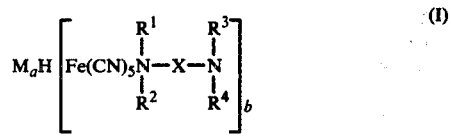

in which
M represents an alkali metal ion, alkaline earth metal ion, heavy metal ion or ammonium ion or a proton,
$R^1$, $R^2$, $R^3$ and $R^4$, independently of one another, each represent hydrogen, alkyl, hydroxyalkyl, cycloalkyl, optionally substituted aryl or aralkyl or
$R^1$, together with $R^2$, and/or $R^3$, together with $R^4$, represent an alkylene group, a bis-alkylene ether group or a bis-alkylene thioether group or, together with the adjacent nitrogen atom, form an unsaturated heterocyclic ring, or
$R^2$ and $R^4$ each represent hydrogen, alkyl or hydroxyalkyl and at the same time
$R^1$ and $R^3$ together represent an alkylene group,
X represents an alkylene group, hydroxyalkylene group, cycloalkylene group, bis-alkylenecycloalkylene group, bis-alkylene ether group, trisalkylene diether group, bis-alkylene thioether group or bis-alkyleneamino group,
a represents 1 or 2 and
b represents 1, 2, 3 or 4,
or a hydrate of a prussiate of the formula (I), in admixture with a solid or liquefid gaseous diluent or carrier or in admixture with a liquid diluent or carrier containing a surface-active agent.

2. A composition according to claim 1 wherein in said prussiate of the formula (I)
M represents sodium, potassium, magnesium, calcium, barium, ammonium or hydrogen;
$R^1$ represents hydrogen, straight-chain or branched alkyl or hydroxyalkyl each with 1 to 6 carbon atoms, cyclopentyl, cyclohexyl, benzyl or phenyl which is optionally substituted by alkyl with 1 to 4 carbon atoms and/or halogen, and $R^2$, $R^3$ and $R^4$, which need not be identical, each represent hydrogen, straight-chain or branched alkyl with 1 to 6 carbon atoms, or phenyl which is optionally substituted by alkyl with 1 to 4 carbon atoms and/or halogen; or $R^1$, together with $R^2$, and/or $R^3$ together with $R^4$, represent a straight-chain or branched alkylene group with 1 to 7 carbon atoms or a bis-alkylene ether or bis-alkylene thioether group each with 1 to 4 carbon atoms per alkylene grouping; or $R^1$ and $R^2$ and/or $R^3$ and $R^4$ represent, together with the adjacent nitrogen atom, a five-membered to seven-membered unsaturated heterocyclic ring in which up to 3 carbon atoms can be replaced by nitrogen; or $R^1$ and $R^3$ together represent a straight-chain or branched alkylene group with 1 to 3 carbon atoms;

X represents an alkylene or hydroxyalkylene group with 1 to 15 carbon atoms, cyclohexylene, a bis-alkylenecyclohexylene group with 1 to 4 carbon atoms per alkylene grouping or a bis-alkylene ether, tris-alkylene diether, bis-alkylene thioether or bis-alkyleneamino group with 1 to 4 carbon atoms per alkylene group;

a represents 1 or 2; and b represents 1, 2 or 3, or a hydrate thereof.

3. A composition according to claim 1 wherein said prussiate has the formula

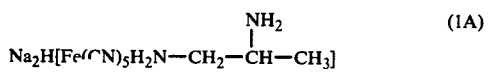 (IA)

4. A composition according to claim 1 wherein said prussiate has the formula

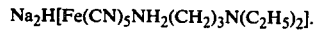

5. A composition according to claim 1 wherein said prussiate has the formula

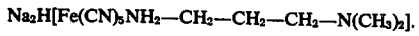

6. A composition according to claim 1 wherein said prussiate has the formula

7. A composition according to claim 1 wherein said prussiate has the formula

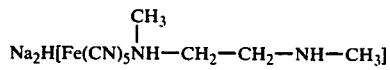

8. A composition according to claim 1 wherein said prussiate has the formula

9. A composition according to claim 1 wherein said prussiate has the formula

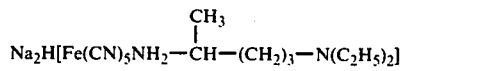

10. A composition according to claim 1 wherein said prussiate has the formula

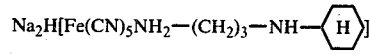

11. A composition according to claim 1 wherein said prussiate has the formula

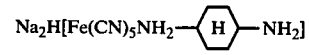

12. A composition according to claim 1 wherein said prussiate has the formula

13. A composition according to claim 1 wherein said prussiate is present in an amount of 0.1 to 95% by weight.

14. A method of supplying plants with micronutrient iron which comprises applying to the plants, or to the substance in which it grows a prussiate of the formula of claim 1 or a hydrate thereof alone or in admixture with a diluent or carrier.

15. A method according to claim 14 wherein said prussiate or its hydrate is applied at a rate of from 0.1 to 100 kg/hectare.

16. A method according to claim 15 wherein said prussiate or its hydrate is applied at a rate of from 1 to 50 kg/hectare.

17. A method according to claim 14 wherein the plant is one suffering from an iron deficiency disease.

18. A method according to claim 14 wherein the plant is a grape or chrysanthemum plant.

19. A method according to claim 14 wherein the plant is one suffering from a deficiency of nutrient ions other than iron which ions are contained in the prussiate of the formula (I) or its hydrate.

20. A plant whenever supplied with the micronutrient content by the method of claim 14.

21. A prussiate of the formula

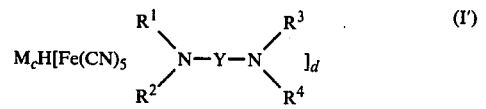 (I')

in which

M represents an alkali metal ion, alkaline earth metal ion, heavy metal ion or ammonium ion or a proton, c represents 1 or 2, d represents 1, 2, 3 or 4, $R^1$, $R^2$, $R^3$ and $R^4$, independently of one another, each represent hydrogen, alkyl, hydroxyalkyl, cycloalkyl, optionally substituted aryl or aralkyl, or $R^1$, together with $R^2$, and/or $R^3$ together with $R^4$, represent and alkylene, bis-alkylene ether or a bisalkylene thioether group or, together with the adjacent nitrogen atom, for an unsaturated heterocyclic ring, or $R^2$ and $R^4$ each represent hydrogen, alkyl or hydroxyalkyl and at the same time $R^1$ and $R^3$ together represent an alkylene group, and Y represents an alkylene group, hydroxyalkylene group, cycloalkylene group, bis-alkylenecycloalkylene group, bis-alkylene ether group, tris-alkylene diether group, bis-alkylene thioether group or bis-alkyleneamino group, except that Y does not represent a —CH$_2$—CH$_2$— group when R$^1$, R$^2$, R$^3$ and R$^4$ each represent hydrogen and their hydrates.

22. A prussiate according to claim 21 having the formula $$Na_2H[Fe(CN)_5H_2N-CH_2-\underset{\underset{NH_2}{|}}{CH}-CH_3] \quad (1A)$$

23. A prussiate according to claim 21 having the formula

Na$_2$H[Fe(CN)$_5$NH$_2$(CH$_2$)$_3$N(C$_2$H$_5$)$_2$].

24. A prussiate according to claim 21 having the formula

Na$_2$H[Fe(CN)$_5$NH$_2$-CH$_2$-CH$_2$-CH$_2$-N(CH$_3$)$_2$].

25. A prussiate according to claim 21 having the formula

Na$_2$H[Fe(CN)$_5$NH$_2$(CH$_2$)$_3$NH-CH$_3$].

26. A prussiate according to claim 21 having the formula

Na$_2$H[Fe(CN)$_5$NH$_2$-CH$_2$-CH$_2$-NH-CH$_3$].

27. A prussiate according to claim 21 having the formula

Na$_2$H[Fe(CN)$_5$NH$_2$-CH$_2$-CH$_2$-NH-CH$_2$-CH$_2$-NH$_2$].

28. A prussiate according to claim 21 having the formula $$Na_2H[Fe(CN)_5\underset{\underset{CH_3}{|}}{N}H-CH_2-CH_2-NH-CH_3]$$

29. A prussiate according to claim 21 having the formula

Na$_2$H[Fe(CN)$_5$NH$_2$(CH$_2$)$_4$-NH$_2$].

30. A prussiate according to claim 21 having the formula

Na$_2$H[Fe(CN)$_5$NH$_2$(CH$_2$)$_6$-NH$_2$].

31. A prussiate according to claim 21 having the formula $$Na_2H[Fe(CN)_5NH_2-\underset{\underset{CH_3}{|}}{CH}-(CH_2)_3-N(C_2H_5)_2]$$

32. A prussiate according to claim 21 having the formula

Na$_2$H[Fe(CN)$_5$NH$_2$—(CH$_2$)$_3$—NH—⟨H⟩]

33. A prussiate according to claim 21 having the formula

Na$_2$H[Fe(CN)$_5$NH$_2$—⟨H⟩—NH$_2$]

* * * * *

UNITED STATES PATENT AND TRADEMARK OFFICE
CERTIFICATE OF CORRECTION

PATENT NO. : 4,141,714
DATED : February 27, 1979
INVENTOR(S) : MUES et al.

It is certified that error appears in the above-identified patent and that said Letters Patent are hereby corrected as shown below:

Column 1, line 31, "weekly" should read -- weakly --.

Column 3, line 3, "stability" should read -- suitability --.

Column 6, line 52, "a" should read -- an -- in first occurrence.

column 7, line 60, "psssess" should read -- possess --.

Column 7, line 64, "cerals" should read -- cereals --.

Column 8, line 1, "goosebery" should read -- gooseberry --.

Column 8, line 32, "cxample" should read -- example --.

Column 8, line 46, "syntetic" should read -- synthetic --.

Column 12, line 3, "follos" should read -- follows --.

Column 12, line 59, claim 1, "liquefid" should read -- liquefied --.

Claim 3, column 13, line 35, formula is not clear, after "$Na_2H$" the formula should read -- $[Fe(CN)_5...$ --.

UNITED STATES PATENT AND TRADEMARK OFFICE
CERTIFICATE OF CORRECTION

PATENT NO. : 4,141,714

DATED : February 27, 1979

INVENTOR(S) : MUES et al.

It is certified that error appears in the above—identified patent and that said Letters Patent are hereby corrected as shown below:

Column 14, line 57, claim 21, "and" should read -- an --.

Column 14, line 57-58, claim 21, "bi-salkylene" should read -- bis-alkylene --.

Signed and Sealed this

Nineteenth Day of June 1979

[SEAL]

Attest:

RUTH C. MASON
Attesting Officer

DONALD W. BANNER
Commissioner of Patents and Trademarks